United States Patent [19]

Chasanoff

[11] Patent Number: 4,655,707
[45] Date of Patent: Apr. 7, 1987

[54] LIGHT, CONTINUOUS FORCE ORTHODONTIC APPLIANCE AND METHOD

[76] Inventor: Daniel Chasanoff, Main St., New City, N.Y. 10956

[21] Appl. No.: 717,284

[22] Filed: Mar. 28, 1985

[51] Int. Cl.⁴ .............................................. A61C 7/00
[52] U.S. Cl. ....................................................... 433/9
[58] Field of Search ................................ 433/8, 9, 11

[56] References Cited

U.S. PATENT DOCUMENTS

| | | | |
|---|---|---|---|
| 2,023,849 | 12/1935 | McCoy | 433/11 |
| 3,055,111 | 9/1962 | Kesling | 433/17 |
| 3,797,115 | 3/1974 | Silverman | 433/9 |
| 3,987,547 | 10/1976 | Moss | 433/11 |

*Primary Examiner*—Robert Peshock
*Attorney, Agent, or Firm*—Martin Parkinson

[57] ABSTRACT

An orthodontic appliance and method is described for the correction of malocclusions of teeth. Light, continuous force, with torque being absent, is applied to the dental arch. Round arch wires are secured within brackets having symmetrically and continuously curved grooves. Under the influence of elastomerically applied force, the arch wire guides the teeth into a pre-selected alignment with no torquing forces being necessary.

9 Claims, 8 Drawing Figures

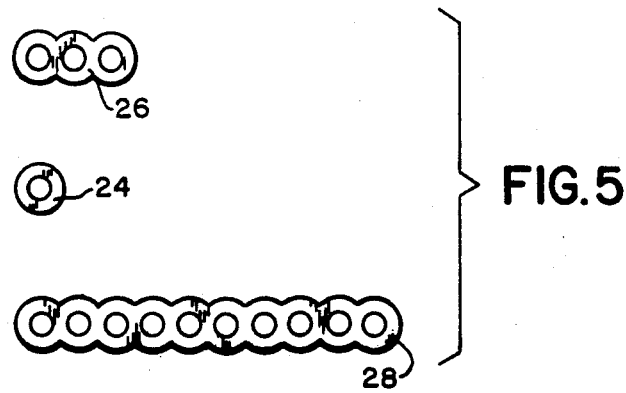
FIG.5
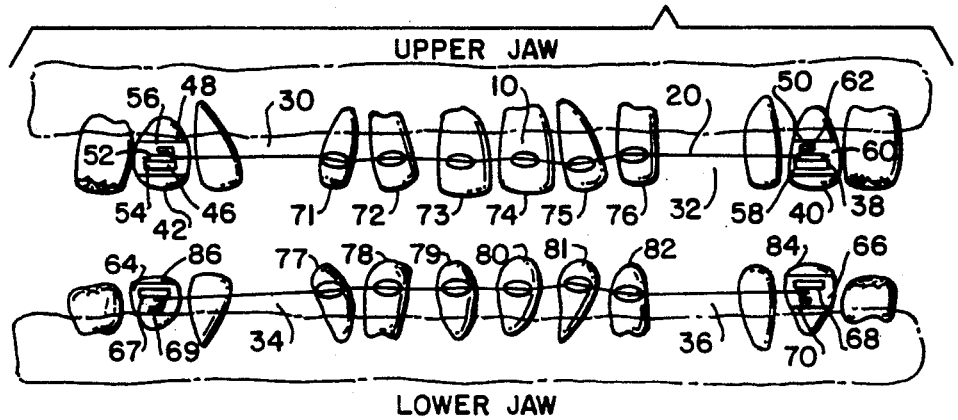
FIG.6
FIG.7
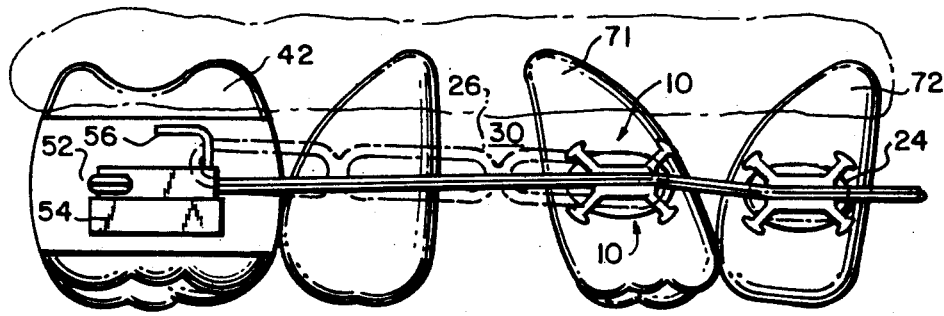

LIGHT, CONTINUOUS FORCE ORTHODONTIC APPLIANCE AND METHOD

BACKGROUND OF THE INVENTION

The present invention relates to the correction of malocclusion of teeth and more particularly to an appliance and method which utilizes light, continuous forces, virtually absent any torque, to accomplish these corrections.

An almost limitless variety of misalignments of teeth, deviating from what is considered normal for a pleasing facial appearance and for eating food properly, is encountered in orthodontic practice. Using current methods and appliances it has been found possible to move teeth bodily in nearly all directions. For example, teeth may be moved mesially (towards the midline of the mouth) or distally (away from the midline of the mouth), occlusally (towards the biting surfaces), gingivally (towards the gums), lingually (towards the tongue), or buccally (towards the cheek). A number of orthodontic appliances and methods are described in "Begg Orthodontic Theory and Technique"—Chapters 6 and 7 (1965—W. B. Saunders Company), the disclosure of which is hereby incorporated by reference.

In a typical procedure designed to correct malocclusions a wire usually referred to as an arch wire is placed across the dental arch of the upper teeth, and a second arch wire is placed across the dental arch of the lower teeth. Means are provided for securing the arch wire at each end of the dental arch. These arch wire securing means are usually metal bands placed around a posterior (most backwardly located in the mouth) tooth such as a first or second molar at both ends of both dental arches. The arch wires are further secured and guided across the dental arches by bracket means which are bonded to selected anterior (at or towards the front of the mouth) teeth such as the central and lateral incisors and the cuspids. A single bracket means is usually bonded directly onto the front surface of these teeth.

A major function of the arch wires is to provide a guide for the teeth so that they will move in a preselected direction during the course of treatment.

In this typical given example the arch wires have a second important function. The arch wires together with the securing brackets are designed to apply torque to the various teeth that are to be moved into a more correct alignment. To provide this torquing force the arch wires are rectangular, i.e. a cross section of the wire shows it to be rectangular in shape. The brackets cooperate with the arch wire in producing torque. Each bracket has a rectangular or square groove in order to engage the arch wire. This rectangular or square groove is not just a straight groove, but is placed in the bracket at an angle to the center plane of the bracket, usually a 5° to 10° angle. So now when these brackets are bonded to teeth, and the arch wire is to be placed within the grooves of these brackets, the arch wire must be twisted to gain entrance to the groove which is at a 5° to 10° angle in relation to the arch wire. The arch wire twisted in this manner will attempt to straighten itself out and in so doing torque will be applied to all of the bracketed teeth. Other tooth moving forces are also applied during treatment, such as the use of elastomeric bands attached at various positions to selected teeth. But it is to the use of torque producing rectangular arch wires and brackets with an angled rectangular or square groove that I wish to give particular attention.

In current orthodontic practice it is considered essential in most cases to apply this described torque in order to obtain optimum results. Although dramatic tooth movement can be obtained over a period of time using these appliances and techniques it has been my observation that a number of disadvantages often accompany such treatment. For example, root resorption may occur at the tips of the roots of front teeth, such as the central and lateral incisors, due to the prolonged application of torque. And bone destruction may occur at the gum line (gingival crest), which is known to promote periodontal breakdown. Also, joint problems at the junction of the upper and lower jaw (tempero-mandibular joint) are frequent sequela to these orthodontic procedures. Finally, the aesthetic appearance of the patient is often less than satisfactory since the excessive forces described tend to move the front teeth too far backward in the mouth, giving a pushed in facial appearance.

Accordingly it is an object to provide an appliance and method that will avoid root resorption.

Another object it to provide an appliance and method that will not cause destruction of bone at the gingival crest.

Another object is to provide an appliance and method that will avoid tempero-mandibular joint problems.

Another object is to provide an appliance and method that will improve facial aesthetics.

A further object is to provide an appliance and method to shorten treatment time to the 14 month level, with less patient discomfort and less patient cooperation required.

SUMMARY OF THE INVENTION

In accordance with the instant invention the above and related objects are obtained by using round arch wires, i.e. arch wires which when viewed in cross section, are seen to be round in shape, in conjunction with securing brackets which contain a groove, which is symmetrically and continuously curved about a central axis, for engaging the round arch wire. The groove is positioned transversely throughout the length of the bracket so that the bottom of the curved groove is parallel to, and at a spaced distance from the center line of the bracket. A slot is provided at the top of the groove, extending the entire length of the groove, the slot being sufficiently wide to permit the insertion of the round arch wire within the curved groove. The use of a round arch wire and brackets with symmetrically and continuously curved grooves affects no torque in contrast to the rectangular wire and brackets with mating rectangular or square grooves of the prior art. That is to say when the round arch wire is placed within the curved groove of the bracket without any twisting of the round arch wire being necessary for this engagement, the possibility of applying torque to the bracketed tooth is virtually eliminated. It is also to be noted that the groove within the bracket can be curved in a number of ways and still cooperate satisfactorily with the round arch wire in the elimination of torque. For example, it can be elliptical or circular in shape.

By virtually eliminating torque, patients are treated in a shorter period of time than was previously possible. Relatively rapid movement of teeth is accomplished with the use of light, continuous forces. Round arch wires secured within the symmetrically and continuously curved grooves of the brackets are exclusively employed, completely eliminating the need for the torque producing rectangular arch wires secured by means of brackets with angled, rectangular or square grooves. Treatment time is shortened to the 14 month level with excellent facial aesthetics. Patients experience less discomfort and less pateint cooperation is required. By eliminating torque, root resorption at the anterior teeth is eliminated, together with destruction of bone at the gingival crest, or subsequent tempero-mandibular joint problems.

It is my belief that the use of rectangular arch wires held in place by brackets containing rectangular or square grooves (located within the bracket at an angle which necessitates twisting the rectangular arch wire when it is placed within the rectangular or square groove) inevitably induces excessive orthodontic forces, principally excessive torque at the root of the bracketed teeth. This can cause both tooth-investing tissues and periodontal membranes to be compressed, limiting or cutting off blood supply to these investing tissues and periodontal membranes. Necrosis with subsequent damage to these dental structures then occurs. I believe that the benefits of my invention are obtained by virtually eliminating torque at all phases of treatment. It is also my belief that by maintaining good periodontal blood supply tooth movement is actually greatly facilitated. Bone is rapidly resorbed where pressure is applied and new bone deposited where there is no pressure. Treatment time is reduced and patient comfort is increased.

My complete method and appliance consists of bonding brackets, each containing a symmetrically and continuously curved groove throughout its length, to anterior teeth such as the central and lateral incisors and the cuspids, placing a round arch wire within these brackets, securing each end of the arch wire to posterior teeth such as the molars utilizing means for attachment of the arch wires in place on these teeth, and connecting elastomeric means (for example, elastomeric bands) either entirely around a full dental arch, or a partial dental arch, and, or individual teeth depending on the nature of the case to be treated, and the stage of treatment. It is the function of these elastomeric means to provide most of the pressure required for tooth movement while the round arch wires guide the teeth, without torque and therefore without trauma, into a pre-selected alignment.

BRIEF DESCRIPTION OF THE DRAWINGS

FIG. 5 illustrates a single unit elastomeric band, a 3 unit elastomeric band, and a 10 unit elastomeric band.

FIG. 6 is a schematic illustration of one possible upper human dental arch and one possible lower human dental arch with the brackets and round arch wires of the invention in place.

FIG. 7 is an enlarged section of FIG. 6 illustrating a 3 unit elastomeric band, shown in phantom, connected to a portion of a dental arch, and a single unit elastomeric band, shown in phantom, connected to one tooth.

DESCRIPTION OF THE PREFERRED EMBODIMENT

Figure 1A:
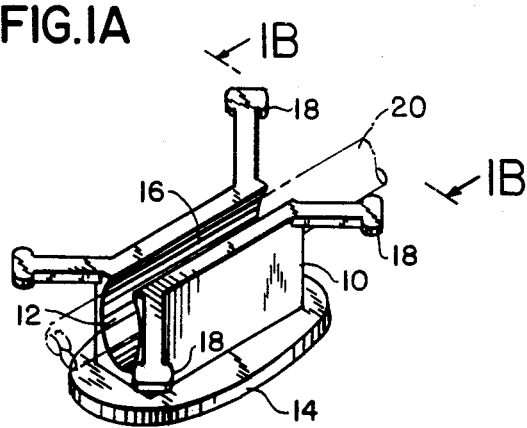
FIG. 1a is a perspective view of the bracket of the invention with a round arch wire illustrated in phantom within the groove of the bracket.
Figure 1B:
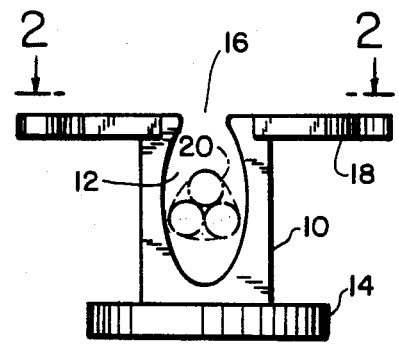
FIG. 1b is a side view of the bracket of the invention.
Figure 2:
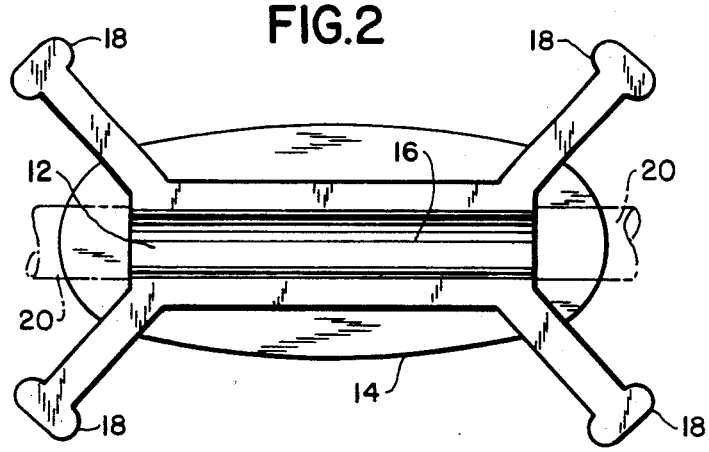
FIG. 2 is a top view of the bracket of the invention.
Figure 3:
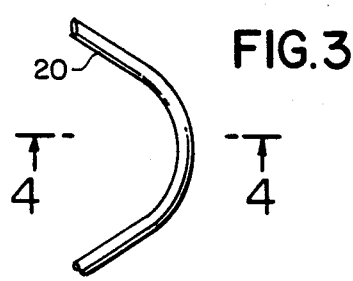
FIG. 3 illustrates a round arch wire.
Figure 4:
FIG. 4 is a cross section of FIG. 3 taken along lines 4—4, illustrating the round shape of the arch wire.

Referring now to FIGS. 1a, 1b, and 2 the bracket 10 contains a symmetrically and continuously curved groove 12 throughout its length. The base 14 of the bracket is the portion that is bonded directly to the front surface of selected teeth during orthodontic procedures. At its top surface the bracket contains a transverse slot 16 which provides an opening to the curved groove 12 within the bracket. The function of the slot 16 and groove 12 is to permit the engagement of round arch wire 20 (FIGS. 1a and 3), so that it may be placed within bracket 10 and thereby be secured in the correct alignment for various treatment procedures. A cross section 24 of round arch wire 20 is shown in FIG. 4.

Groove 12 is preferably placed along the center line of the bracket 10 and similarly slot 16 is preferably placed directly above the center line of the bracket in order to eliminate torque when the round arch wire 20 is placed in the groove within the bracket. It is to be noted that the groove may be curved in a number of ways and still cooperate with the round arch wire in eliminating torque. For example, groove 12 may also have a circular or elliptical shape throughout its length.

Projection 18 extends laterally and at an oblique angle from the bracket. There are four of these projections, one at each edge of the bracket. Their function is to provide a means for securing elastomeric bands, such as elastomeric band 24 shown in FIG. 5.

Referring to FIGS. 6 and 7, the elements for the correct utilization of my invention are shown in an illustrative case. FIG. 6 depicts the teeth of a young patient whose wisdom teeth have not come in as yet and whose first bicuspids on both the left and right sides of both the upper and lower jaws have had to have been removed. Extraction spaces 30 and 32 show where these teeth have been removed in the upper jaw, and extraction spaces 34 and 36 denote the extracted teeth on the lower jaw.

In my method, to treat such a case I first connect double buccal tubes 38 and 46 to molar bands 48 and 50 usually by welding them to these metal bands. The molar bands are then bonded to the first molars 40 and 42. The top tube 52 portion of double buccal tube 46 has a hole throughout its length measuring 0.018 inches I.D. This tube is tipped in towards the midline of the mouth (mesially) by a 6° angle. The bottom tube 54 portion of this double tube has a hole throughout its length which measures 0.045 inches I.D. This bottom tube is not tipped but remains at a 0° angle.

Attached to the top of tube 52 on double buccal tube 46 is a hook 56. Similarly double buccal tube 38 on first molar 40 is equipped with a lower tube 58 having a hole throughout its length which measures 0.045 inches I.D., and an upper tube 60 has a hole throughout its length which measures 0.018 inches I.D. Again top tube 60 is tipped in towards the midline of the mouth (mesially) at an angle of 6°. The bottom tube 58 is not tipped and remains at a 0° angle. The top tube 60 is also equipped with a hook 62. Both hooks 56 and 62 are usually referred to as intermaxillary hooks.

For the lower jaw, single buccal tubes 67 and 68 are attached to molar bands 64 and 66, usually by welding them to these metal bands. The bands are them bonded to the first molars 71 and 72. The single buccal tubes each have a 0.018 inch I.D. hole throughout their length, and are also equipped with intermaxillary hooks 69 and 70. Single and double buccal tubes are well known in orthodontic practice and a further discription is therefore deemed unnecessary.

A bracket 10 is now bonded to each of the frontal surfaces of teeth nos. 71, 72, 73, 74, 75, 76, 77, 78, 79, 80, 81 and 82. I now fit a round arch wire 20 across the dental arch of the upper jaw and a second one across the dental arch of the lower jaw. For both arches I use a 0.0175 inch diameter multitwist round arch wire. In the case of the upper jaw the arch wire is placed within the grooves of the brackets bonded to teeth nos. 71, 72, 73, 74, 75 and 76. Then the arch wire is inserted into the hole in the top tube 52 of double buccal tube 46, and on the other side of the mouth the arch wire is inserted into the hole in the top tube 60 of double buccal tube 38. Both ends of the arch wire are then bent to secure the wire to the buccal tubes. Similarly for the lower jaw an identical round arch wire is fitted into all the grooves in the brackets bonded to teeth nos. 77, 78, 79, 80, 81 and 82, and the arch wire ends are then inserted into the holes in single buccal tubes 67 and 68. The arch wire ends are then bent to secure the arch wire to the buccal tubes. Multitwist arch wire of varying diameter are well known to the art and a further description is therefore deemed unnecessary.

I now connect a 3 unit elastomeric band 26 (FIG. 5) between the first molars 42 and 40 and the cuspids 71 and 76 of the upper jaw. The end of one band is connected to intermaxillary hook 56 with its other end connected to projections 18 (FIG. 2) on bracket 10 which is bonded to cuspid 71. One end of a second 3 unit elastomeric band is connected to intermaxillary hook 62, and the other end to the projections of the bracket 10 bonded to cuspid 76 on the left side of the upper jaw.

Two identical 3 unit elastomeric bands are employed in the same manner on the lower jaw between first molar 86 and cuspid 77; and between first molar 84 and cuspid 82.

A single elastomeric band 24 (FIG. 5) is used on each of the front teeth that require some adjustment (rotational movement), and when there is adequate room in the dental arches to make the adjustments.

A 3 unit elastomeric band 26 is shown in phantom in FIG. 7 connecting the first molar 42 to the cuspid 71 using intermaxillary hook 56 on the molar, and bracket 10 on the cuspid. A single elastomeric band 24 is illustrated in phantom encircling the bracket 10 and tieing in the arch wire on the lateral incisor 72 in FIG. 7.

In this case I employ single elastomeric bands on the central incisors 73 and 74, and the lateral incisors 72 and 75 of the upper jaw. On the lower jaw I place single elastomeric bands on central incisors 79 and 80, and lateral incisors 77 and 81.

In my method the teeth are now gradually moved by the elastomeric bands into the desired pre-selected alignment without the use of torque. The round arch wires, held in place by brackets with symmetrically and continuously curved grooves, serve to guide the teeth into correct alignment, again without torquing forces being applied.

All of the elastomeric bands are removed and replaced with new ones once every four weeks. And once every eight weeks the arch wires are replaced with new ones in this gradual, ongoing process of correcting the alignment of the teeth. The above described elastomeric bands are manufactured by Unitek Corporation, Monrovia, Calif. and are well known in orthodontic procedures.

When the extraction spaces 30 and 32 in the upper jaw, and extraction spaces 34 and 36 in the lower jaw have been almost completely closed the 0.0175 inch diameter round arch wires 22 (FIG. 3) are removed, and replaced with round arch wires with a 0.016 inch diameter (not shown). This is a stiffer wire than the 0.0175 inch diameter arch wire used so far in the treatment, and aids in obtaining a finer guidance of final tooth movement to complete the treatment. At the same time in the illustrative case a 10 unit elastomeric band 28 is connected across the dental arch of the upper jaw, one end being connected to intermaxillary hook 56, and the other end to intermaxillary hook 62. Similarly a 10 unit elastomeric band is connected to the dental arch of the lower jaw, connected at one end to intermaxillary hook 69, and at the other end to intermaxillary hook 70. Where extraction of teeth has not been necessary, and therefore extraction spaces 30, 32, 34 and 36 illustrated in FIG. 6 are not present, I would use a 12 unit elastomeric band (not shown) on the dental arch of the upper jaw, and a second 12 unit elastomeric band on the dental arch of the lower jaw.

The case is completed after approximately 3 changes of the 0.016 inch diameter arch wires and 6 changes of the elastomeric bands. The case is now debanded, i.e. all of the above appliances including buccal tubes, arch wires, brackets and elastomeric bands are removed from the patients mouth. About fourteen months from the initial arch wire emplacement to this point in the treatment is required. This contrasts with conventinal orthodontic practice which usually takes two to two and one half years to reach this same stage.

Upper arch retainers are now made, such as an upper Hawley appliance (not shown) which is a standard orthodontic retention appliance designed to aid in retaining the upper teeth in the positions they have been moved to during treatment. For the lower arch I generally use a cuspid to cuspid spring retainer (not shown) to maintain the position of the lower anterior (front) teeth and the rotation corrections I have achieved during treatment.

Both the upper Hawley appliance and the cuspid to cuspid spring retainer are worn for about a year to prevent relapse from occurring. The upper Hawley appliance, and the cuspid to cuspid spring retainer are well known in orthodontic practice and form no part of this invention.

While the present invention has been disclosed in connection with the preferred embodiment shown and described in detail, various modifications and improvements thereon will become readily apparent to those skilled in the art. Accordingly, the spirit and scope of the present invention is to be limited only by the following claims.

I claim:

1. An appliance for correcting malocclusions in teeth which comprises:
    (A) An arch wire means, having a round cross section, for connection across a pre-determined dental arch; and
    (B) A bracket means, said bracket means having a body with a base, upstanding side walls extending from said base said side wall having projection means extending laterally at an oblique angle from said bracket means so that an elastomeric means may be secured to said bracket means, said upstanding side wall defining within said body a transverse, symmetrically and continuously curved groove, said groove having a slot at its top which extends along the length of said groove, such that when said base of said bracket means is bonded to selected teeth, said arch wire may be placed within said groove to assist said arch wire in maintaining a desired position for guiding said teeth into a pre-selected alignment without torque.

2. An appliance as recited in claim 1 in which said groove in said bracket is circular in shape.

3. An appliance as recited in claim 1 in which said groove in said bracket is elliptical in shape.

4. An appliance as recited in claim 1 further comprising elastomeric means for connection across said predetermined dental arch, said elastomeric means being anchored at one end to a first pre-selected posterior tooth using means connected to said tooth for engaging said elastomeric means, and said elastomeric means being anchored at its other end to a second pre-selected posterior tooth using means connected to said second tooth for engaging said other end of said elastomeric means, to assist said guiding of said teeth into said pre-selected alignment.

5. An appliance as recited in claim 1 further comprising an elastomeric means for connection across a portion of said predetermined dental arch, said elastomeric means being anchored at one end to a first pre-selected tooth using means connected to said first tooth for engaging said end of said elastomeric means, and said elastomeric means being anchored at its other end to a second pre-selected tooth at a spaced distance from said first tooth using means connected to said second tooth for engaging said other end of said elastomeric means, to assist said guiding of said teeth into said pre-selected alignment.

6. An appliance as recited in claim 1 further comprising an elastomeric means for connection to a single tooth, said elastomeric means being placed around said bracket bonded to said tooth, and said elastomeric means being held in place by means connected to said bracket for engaging said elastomeric means, to assist said guiding of said tooth into said pre-selected alignment.

7. A bracket for securing and guiding an arch wire in orthodontic precedures without torque, which comprises: a body with a base for bonding to the surface of a tooth, upstanding side walls extending from said base said side wall having projection means extending laterally at an oblique angle from said bracket means so than an elastomeric means may be secured to said bracket means, said upstanding side wall defining within said body a transverse, symmetrically and continuously curved groove, said groove having a slot at its top which extends along the length of said groove, such that said arch wire may be placed within said groove.

8. A bracket as recited in claim 7 in which said groove is circular in shape.

9. A bracket as recited in claim 7 in which said groove is elliptical in shape.

* * * * *